(12) United States Patent
Mackey

(10) Patent No.: US 7,515,690 B2
(45) Date of Patent: Apr. 7, 2009

(54) RADIOLOGICAL SCANNING ORIENTATION INDICATOR

(76) Inventor: J. Kevin Mackey, 12021 Wilshire Blvd., #888, Los Angeles, CA (US) 90025

( * ) Notice: Subject to any disclaimer, the term of this patent is extended or adjusted under 35 U.S.C. 154(b) by 10 days.

(21) Appl. No.: 11/429,004

(22) Filed: May 5, 2006

(65) Prior Publication Data

US 2007/0269016 A1 Nov. 22, 2007

(51) Int. Cl.
*A61B 6/04* (2006.01)
*A61B 6/08* (2006.01)

(52) U.S. Cl. ...................... 378/163; 378/205

(58) Field of Classification Search ............ 378/20, 378/162, 163, 170, 177, 205
See application file for complete search history.

(56) References Cited

U.S. PATENT DOCUMENTS

| | | | |
|---|---|---|---|
| 3,867,634 A * | 2/1975 | Hounsfield ............ 378/18 |
| 4,319,136 A | 3/1982 | Jinkins |
| 4,341,220 A | 7/1982 | Perry |
| 4,581,752 A * | 4/1986 | De Luca ............ 378/62 |
| 4,583,538 A * | 4/1986 | Onik et al. ............ 606/130 |
| 4,698,836 A * | 10/1987 | Minasian ............ 378/162 |
| 4,860,331 A * | 8/1989 | Williams et al. ........ 378/163 |
| 4,971,060 A | 11/1990 | Schneider et al. |
| 5,189,689 A | 2/1993 | Fabian |
| 5,232,452 A | 8/1993 | Russell et al. |
| 5,583,343 A * | 12/1996 | Dilmanian et al. ...... 250/475.2 |
| 5,991,701 A * | 11/1999 | Triano ............ 702/150 |
| 5,999,591 A | 12/1999 | Kobayashi et al. |
| 6,096,048 A | 8/2000 | Howard, III et al. |
| 6,122,541 A | 9/2000 | Cosman et al. |
| 6,178,229 B1 | 1/2001 | Ko |
| 6,246,900 B1 * | 6/2001 | Cosman et al. ............ 600/426 |
| 6,374,135 B1 | 4/2002 | Bucholz |
| 6,501,981 B1 * | 12/2002 | Schweikard et al. ........ 600/427 |
| 6,527,443 B1 | 3/2003 | Vilsmeier et al. |
| 6,567,687 B2 * | 5/2003 | Front et al. ............ 600/426 |
| 6,662,036 B2 | 12/2003 | Cosman |
| 6,678,353 B2 | 1/2004 | Graumann et al. |
| 2002/0087101 A1 * | 7/2002 | Barrick et al. ............ 600/587 |
| 2002/0102214 A1 * | 8/2002 | Briley-Saebo et al. ..... 424/9.36 |
| 2003/0206614 A1 * | 11/2003 | Kendrick et al. ............ 378/205 |
| 2004/0008810 A1 * | 1/2004 | Nelson et al. ............ 378/19 |
| 2004/0216211 A1 * | 11/2004 | Ruane ............ 2/69 |
| 2005/0213713 A1 * | 9/2005 | Cadwalader et al. ........ 378/203 |
| 2006/0184014 A1 * | 8/2006 | Pfeiler ............ 600/426 |
| 2006/0241406 A1 * | 10/2006 | Noujeim ............ 600/426 |
| 2007/0060799 A1 * | 3/2007 | Lyon et al. ............ 600/300 |

* cited by examiner

*Primary Examiner*—Edward J Glick
*Assistant Examiner*—Anastasia Midkiff
(74) *Attorney, Agent, or Firm*—David A. Belasco; Belasco Jacobs & Townsley, LLP

(57) ABSTRACT

A radiological imaging orientation indicator includes a linear indication member having a substantially uniform cross-sectional shape and means for positioning the indication member adjacent a patient's body. When the indication member is located adjacent the patient's body and a sectional scanning image is produced, a cross-section of the indication member will appear in the scanning image, indicating an orientation of the patient's body with respect to the scanning image. The linear indication member is in the form of either of an extruded letter, number and symbol which may be hollow with one or more liquids trapped inside to indicate vertical orientation. The means for positioning the indication member include pants, vests, caps, visors, eyeglass frames, sandals, gloves and collars that can only be attached to a patient's body in one way, thereby preventing confusion in determining the orientation of a scanning image. The invention includes orientation indicators for standard X-rays.

1 Claim, 6 Drawing Sheets

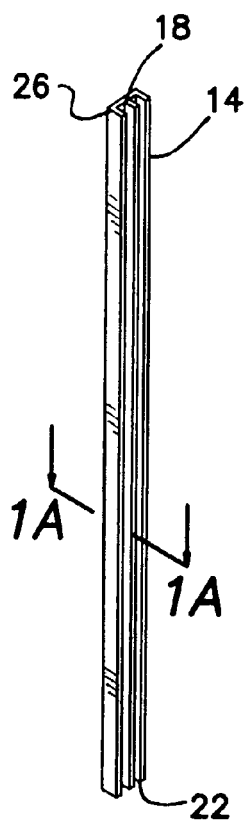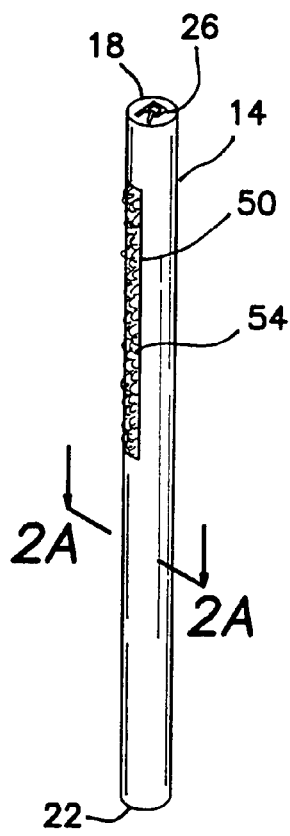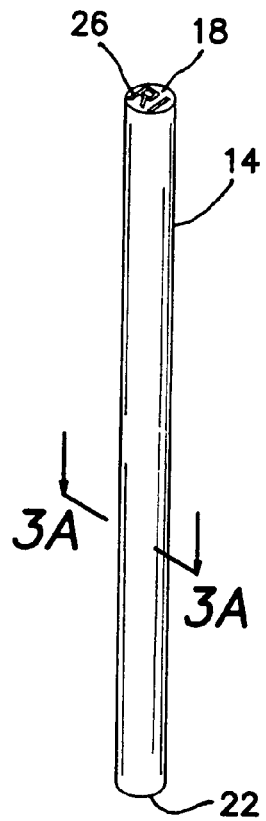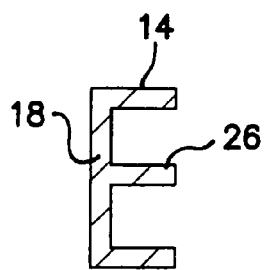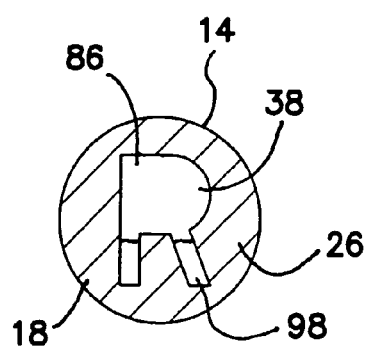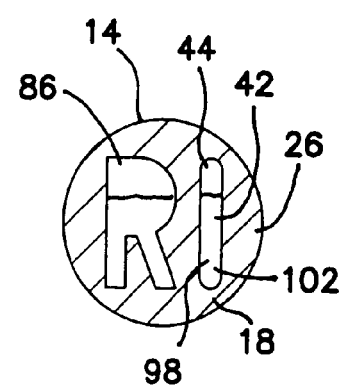

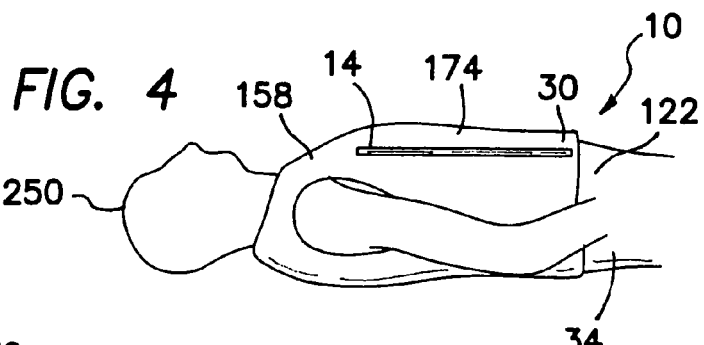
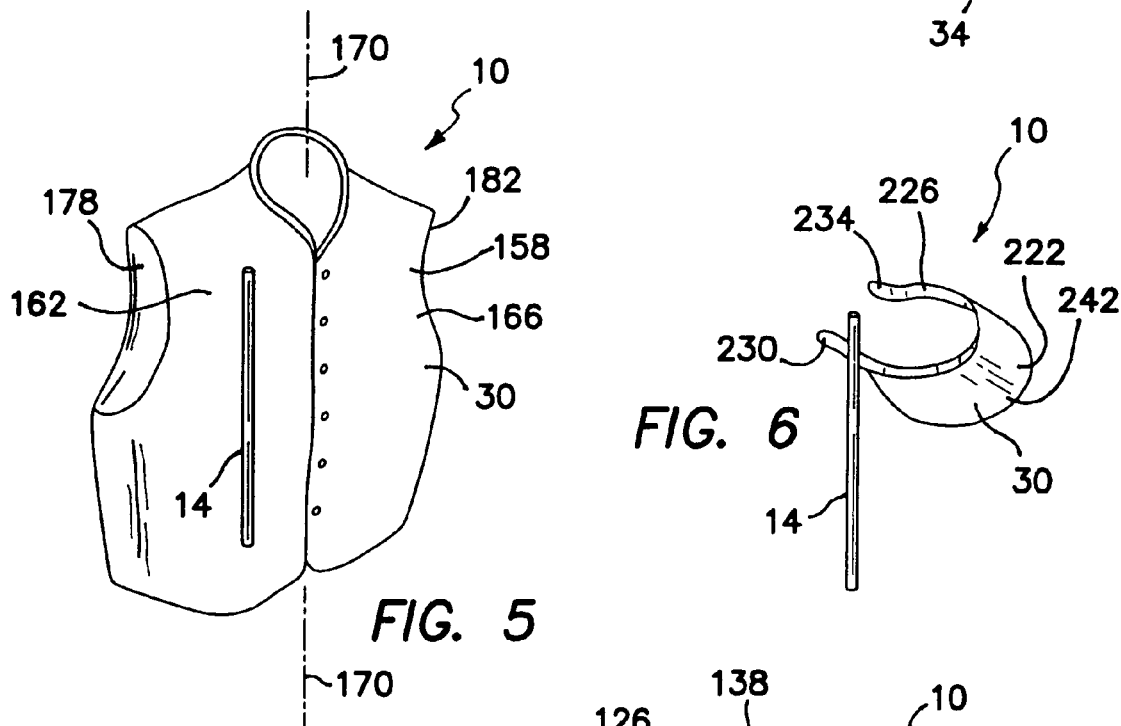
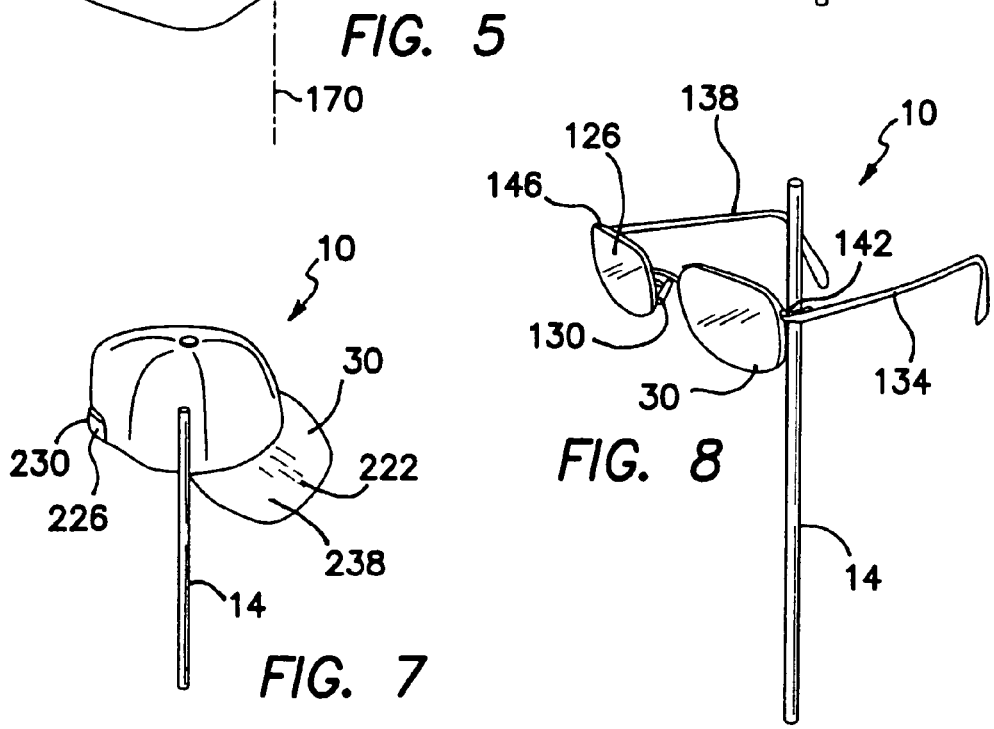

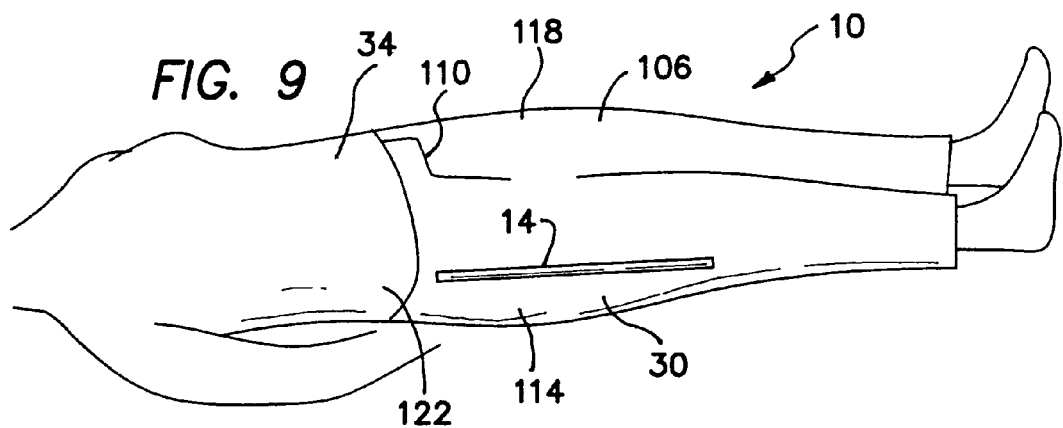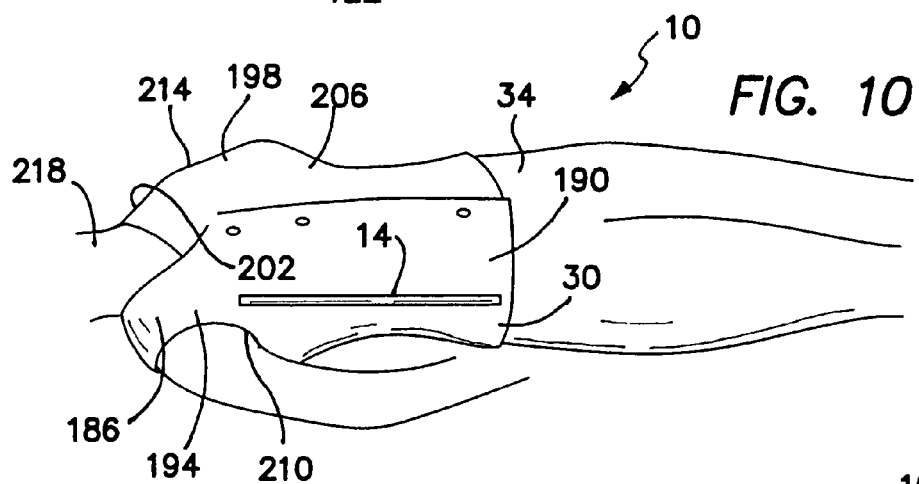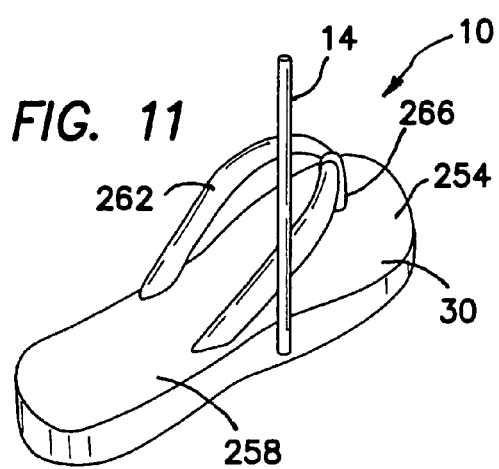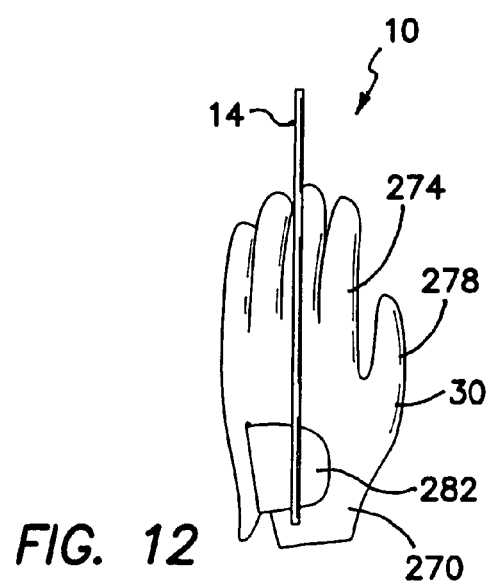

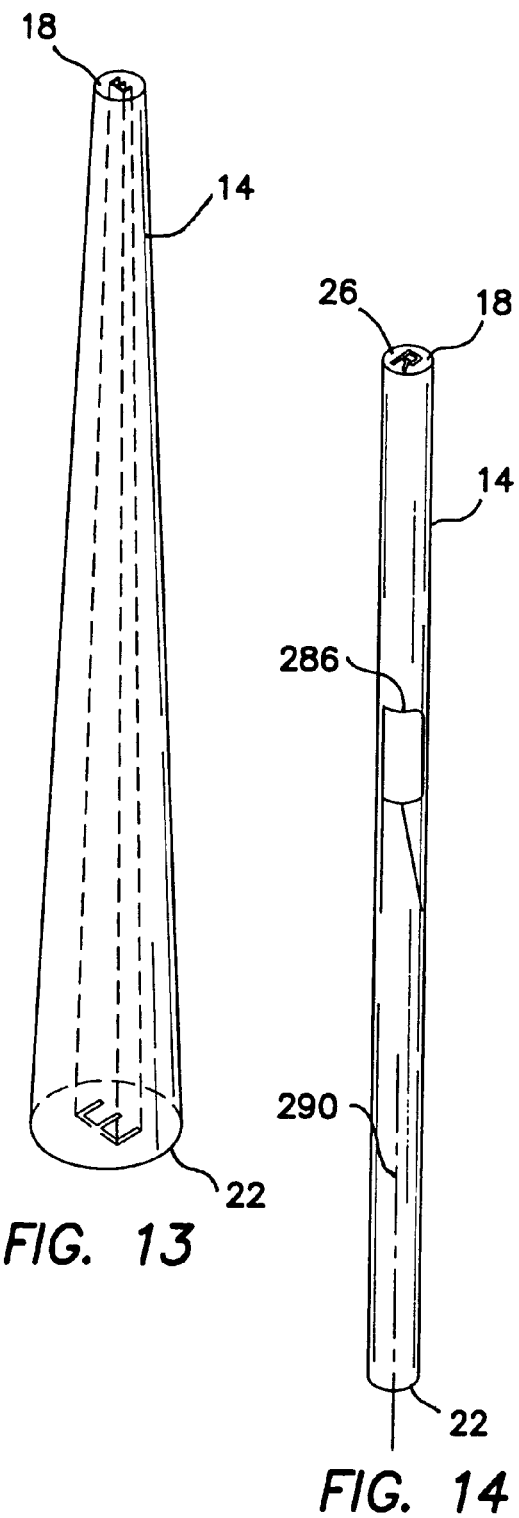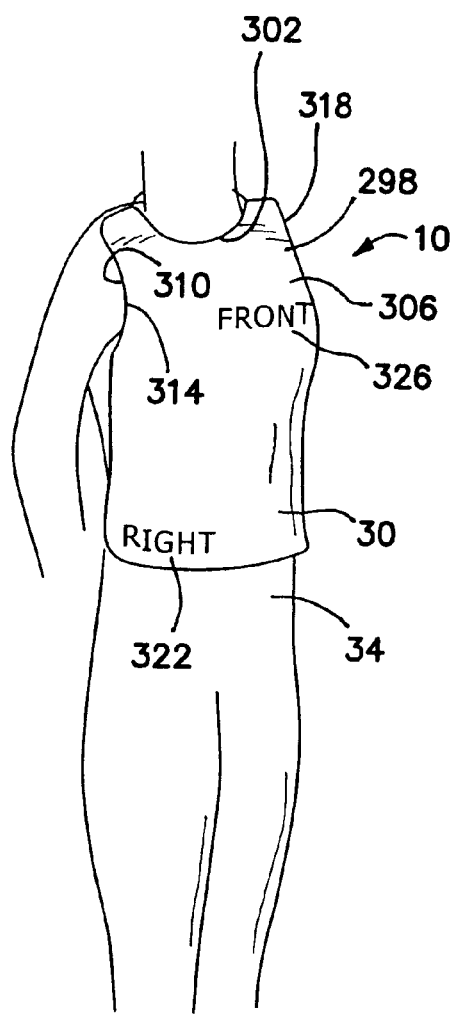
FIG. 13
FIG. 14
FIG. 15

RADIOLOGICAL SCANNING ORIENTATION INDICATOR

FIELD OF INVENTION

The invention pertains to radiological scanning systems. More particularly, the invention relates to devices for determining with precision the orientation of a patient undergoing a scanning or other radiographic procedure.

BACKGROUND OF THE INVENTION

Modern radiological scanning systems are capable of providing detailed imaging of a patient's body in the nature of a cross-sectional view. That is, these systems can provide a "thin slice" image of various organs and portions of the body taken at different orientations including different elevations and from different points of view. These images require annotation of orientation, including sidedness, for left versus right orientation. Typical systems involve a patient being introduced into a scanning system on a sliding horizontal platform, either head first or feet first. Presently the system operator will key in the orientation of the patient on the platform and the resulting images will bear an indication of this orientation. Often major surgery is performed based upon these scan images and the orientation indication is critical to performing the surgery on the correct side of the patient. As the orientation input is under the control of the system operator, errors are possible. If the operator enters "feet first" instead of "head first" the image will be marked incorrectly by the machine. Similar problems can occur when an operator enters "prone" versus "supine."

For example, due to symmetry of anatomy, it is not possible to examine a brain sectional image and determine which side is the left side of the brain and which is the right. An error here could result in surgery on the wrong side of a patient's head. Even for body areas with inherent asymmetry, for example the chest and abdomen, any person born with situs inversus, this anatomy is reversed, leading to confusion and possible errors. To-date, no foolproof system has been developed to determine the orientation used in producing these scanned images. Similarly, with standard X-ray a technician can mislabel left versus right when he manually places a marker on the film cassette.

Various systems have been developed to identify the orientation used in scanning systems. U.S. Pat. No. 6,678,353, issued to Graumann et al., discloses a method applied and an x-ray system for determining a spatial relationship of X-ray datasets measured independently of one another, an x-ray apparatus registers X-ray datasets of a patient and a scale is provided that makes position data available that are identifiable in at least one of the registered dataset. The position data serve for the determination of the spatial relationship between at least two X-ray datasets that were registered from different body portions of the patient.

U.S. Pat. No. 4,583,538, issued to Onik et al. is directed to a method and apparatus which allow for CT guided biopsies of the body. The method is based on the finding of a reference point on the patient's body that exactly correlates to a point on the CT scan. This is accomplished by means of a localization device placed on the patient's skin which can be identified in cross section on the CT scan. Measurements of the localization device on CT scan can then be correlated to the device on the patient.

U.S. Pat. No. 4,319,136, issued to Jinkins disclose a data transfer for cranial computerized tomography images that is substantially form-fitting and dome-shaped. First and second groups of elongated depth markers are positioned in front and in back, diametrically across from each other, and each depth marker extends from the peripheral edge of the cap toward the apex of the cap, the markers are positioned parallel to one another and each marker is graduated in length and terminates at its upper end in an enlargement. A plurality of longitudinal or circumferential markers are positioned between the first and second groups of depth markers and also extend from the peripheral edge of the cap toward the apex of the cap.

U.S. Pat. No. 4,971,060, issued to Schneider et al. is directed to an apparatus worn by a patient to provide a geometric reference for medical diagnostic data obtained from the patient has an element rigidly attachable to the patient, this element being connected to other components which emit a known and recognizable signal during the acquisition of medical diagnostic data, those components being used to establish a geometric reference for the data obtained from the patient. In one embodiment, a bite-down plate having a shape corresponding to the dentition of the patient is held in the mouth of the patient, and is connected to a rigid carrier having markings for geometrically referencing a tomographic image.

In another embodiment, the worn element is a rigid ring worn by the patient as a headband, having a number of length-variable indicators, each of which having a scale, and also being connected to a member having a recognizable shape, or having markings, for a reference in tomographic imaging. Both embodiments can be used with other examination equipment, such as devices for obtaining biomagnetic signals, so that the respective data obtained from multiple examination devices can be geometrically correlated.

U.S. Pat. No. 4,341,220, issued to Perry discloses X-ray detectable fiducial markers are associated with a stereotactic surgery frame. The frame is fixed with respect to a patient's anatomy and defines a predetermined three-dimensional coordinate system in which surgical devices may be precisely positioned. A desired target area of the anatomy is detected in a cross-sectional CT scanner depiction of the combined stereotactic frame and patient anatomy. The target's coordinates with respect to the frame are calculated based on three non-collinear fiducial points also located within the cross-section and having known coordinates both with respect to the frame and with respect to the target. In the exemplary embodiment, detachable fiducial point-defining members are associated with a stereotactic surgical frame.

For example, each member may be a plate having a series of parallel grooves or slots which progressively increase in length from one slot to the next. The frame coordinates of the end points of each slot are predetermined and known. Thus three fiducial points with respect to the frame can be determined by simply counting the number of slots or grooves contained within the cross-sectional depiction and thereby determining which end point is within such cross-section.

It is an objective of the present invention to provide a failsafe method of identifying the orientation of a patient in a scanning procedure, especially sidedness, right versus left. It is a still further objective of the invention to provide this method of identification through apparatus adaptable to various types of scanning procedures. Finally, it is an objective of the present invention to provide such identification through inexpensive and disposable fixtures or apparatus that do not interfere with the scanning procedures.

While some of the objectives of the present invention are disclosed in the prior art, none of the inventions found include all of the requirements identified.

SUMMARY OF THE INVENTION

The present invention addresses all of the deficiencies of prior radiological imaging orientation indicator inventions and satisfies all of the objectives described above.

(1) A radiological imaging orientation indicator providing the desired features may be constructed from the following components. A linear indication member is provided. The indication member has a first end, a second end and substantially uniform cross-sectional shape. Means are provided for positioning the indication member adjacent a patient's body to reliably identify the orientation of the body. The shape of the positioning device conforms to the body in only a single orientation, establishing the reference point for the orientation indicator. When the linear indication member is located adjacent the patient's body and a sectional scanning image is produced, a cross-section of the indication member will appear in the scanning image, indicating an orientation of the patient's body with respect to the scanning image.

(2) In a variant of the invention, the indication member is in the form of an extruded letter, number or symbol.

(3) In another variant, the indication member is attached adjacent the patient's body using means selected from the group consisting of looping and hooking fasteners, snaps, buckles, button, zippers, elastic bands and clips.

(4) In still another variant, the indication member includes a first internal cavity. The first cavity extends from a first end of the member to a second end of the member and is in the form of either of a letter, number and symbol. When the linear indication member is located adjacent the patient's body and a sectional scanning image is produced, a cross-section of the indication member and the first cavity in the form of either of the letter, number and symbol will appear in the scanning image, indicating an orientation of the patient's body with respect to the scanning image.

(5) In yet another variant, the first internal cavity is sealed at the first and second ends and includes at least one liquid located in it. The liquid indicates vertical orientation of the indication member.

(6) In a further variant, the indication member includes a second internal cavity. The second cavity extends from a first end of the member to a second end of the member. The second cavity is partially filled with at least one liquid and is sealed at the first and second ends to prevent loss of the liquid. When the linear indication member is located adjacent the patient's body and a sectional scanning image is produced, a cross-section of the indication member and the second cavity will appear in the scanning image, indicating an orientation of the patient's body with respect to the scanning image, the cross-section of the second cavity indicating vertical orientation of the indication member. The type of liquid in each cavity may be the same or different.

(7) In still a further variant, the means for positioning the indication member adjacent the patient's body includes a pair of pants. The pants have a front closure means, a first side and a second side and are positionable upon the patient's body in only a single orientation. The indication member is attached to the first side. The pants are located on the patient's body with the indication member positioned adjacent an identified side of the patient's body. When the linear indication member is positioned adjacent the patient's body and a sectional scanning image is produced, a cross-section of the indication member will appear in the scanning image, indicating an orientation of the patient's body with respect to the scanning image.

(8) In yet a further variant, the means for positioning the indication member adjacent the patient's body includes a face-mounted frame. The frame has nose-mounted portion, first and second ear-mounted portions attached to opposite sides of the nose-mounted portion and is positionable upon a patient's face in only a single orientation. The indication member is attached to the first ear-mounted portion. The face-mounted frame is located on the face of the patient with the indication member located adjacent an identified side of the patient's body. When the linear indication member is located adjacent the patient's body and a sectional scanning image is produced, a cross-section of the indication member will appear in the scanning image, indicating an orientation of the patient's body with respect to the scanning image.

(9) In another variant of the invention, the means for positioning the indication member adjacent the patient's body includes a vest. The vest has first and second chest panels. The chest panels extend outwardly from either side of a rear centerline and curve inwardly over a patient's chest. The first and second chest panels have first and second arm holes, respectively. The indication member is attached to the first chest panel. The vest is located on the patient's body with the indication member located adjacent an identified side of the patient's body. When the linear indication member is located adjacent the patient's body and a sectional scanning image is produced, a cross-section of the indication member will appear in the scanning image, indicating an orientation of the patient's body with respect to the scanning image. This embodiment of the invention also includes a shoulder mounted means for positioning the indication member adjacent the patient's body.

(10) In still another variant, the first and second chest panels are removably fastened together.

(11) In yet another variant, the means for positioning the indication member adjacent the patient's body includes a chest-mounted garment. The garment has a front panel. The front panel has a first side, a second side, an inner surface, an outer surface and first and second arm notches. The indication member is attached to the outer surface at the first side. The chest-mounted garment is located on a chest of the patient with the indication member located adjacent an identified side of the patient's body. When the linear indication member is located adjacent the patient's body and a sectional scanning image is produced, a cross-section of the indication member will appear in the scanning image, indicating an orientation of the patient's body with respect to the scanning image.

(12) In a further variant, the means for positioning the indication member adjacent the patient's body includes a head-mounted positioning device. The head-mounted device has at least a partial head-encircling band. The band has a first portion and an opposite second portion and either a cap with a bill or a visor attached to the band between the first portion and the second portion. Either the cap with a bill or the visor is aligned over a nose of the patient. The indication member is attached to the first portion. The head-mounted positioning device is located on a patient's head with the indication member located adjacent an identified side of the patient's body. When the linear indication member is located adjacent the patient's body and a sectional scanning image is produced, a cross-section of the indication member will appear in the scanning image, indicating an orientation of the patient's body with respect to the scanning image.

(13) In still a further variant, the means for positioning the indication member adjacent the patient's body includes a foot-mounted positioning device. The foot-mounted device has a foot platform and a retaining upper attached to the platform. The upper has an attachment thong formed to fit between a large toe and other toes of only one foot of a patient. The indication member is attached to the foot-mounted positioning device and extends upwardly from it. The foot-mounted positioning device is located on the patient's foot with the indication member located adjacent an identified side of the patient's body. When the linear indication member is located adjacent the patient's body and a sectional scanning image is produced, a cross-section of the indication member will appear in the scanning image, indicating an orientation of the patient's body with respect to the scanning image.

(14) In yet a further variant, the means for positioning the indication member adjacent the patient's body includes a hand-mounted positioning device. The hand-mounted device has a palm cover, thumb opening and a retaining strap. The strap is attached across a back of a patient's hand. The hand-mounted device is shaped to fit only one hand of the patient. The indication member is attached to the hand-mounted positioning device and extends downwardly from it. The hand-mounted positioning device is located on the patient's hand with the indication member located adjacent an identified side of the patient's body. When the linear indication member is located adjacent the patient's body and a sectional scanning image is produced, a cross-section of the indication member will appear in the scanning image, indicating an orientation of the patient's body with respect to the scanning image. The hand-mounted device could be in the form of a glove or a mitten.

(15) In another variant, the indication member varies in cross-sectional width from the first end to the second end. The variation indicates a relative position of the sectional scanning image with respect to the patient's body.

(16) In still another variant, a two dimensional orientation symbol is located orthogonally to a long axis of the indication member. The symbol appears in either a standard radiographic image or a computed tomography pilot image also known as a scout image.

(17) In yet another variant, the means for positioning the indication member adjacent the patient's body includes a face-mounted positioning device. The face-mounted positioning device is sized and shaped to fit over at least a portion of a face of a patient in only a single orientation and has a first side edge and a second side edge. The indication member is attached adjacent to the first side edge. The face-mounted positioning device is located on the patient's face with the indication member located adjacent an identified side of the patient's body. When the linear indication member is located adjacent the patient's body and a sectional scanning image is produced, a cross-section of the indication member will appear in the scanning image, indicating an orientation of the patient's body with respect to the scanning image.

(18) In a final variant, a radiological imaging indicator, includes an identifying collar. The collar has a neck recess, an outer surface, an inner surface, first and second arm notches, at least a body side indicator. The indicator is visible on radiological images. The identifying collar is located on a chest of the patient with the inner surface located against the chest and the arm notches about arms of the patient. When the patient receives a chest x-ray, the body side indicator will appear in the x-ray. This embodiment of the invention also includes a shoulder mounted means for positioning the radiological imaging indicator adjacent the patient's body.

An appreciation of the other aims and objectives of the present invention and an understanding of it may be achieved by referring to the accompanying drawings and the detailed description of a preferred embodiment.

DESCRIPTION OF THE DRAWINGS

FIG. 1 is a perspective view of a linear indication member;

FIG. 1A is a cross-sectional view of the FIG. 1 embodiment taken along the lines 1A-1A;

FIG. 2 is a perspective view of an alternate linear indication member with a hollow internal cavity for containing liquids and a looping attachment means along its length;

FIG. 2A is a cross-sectional view of the FIG. 2 embodiment taken along the lines 2A-2A;

FIG. 3 is a perspective view of an alternate linear indication member with two hollow internal cavity for containing liquids;

FIG. 3A is a cross-sectional view of the FIG. 3 embodiment taken along the lines 3A-3A;

FIG. 4 is a side elevational view of a vest version of the invention illustrating attachment of the linear indication member;

FIG. 5 is a perspective view of the FIG. 4 embodiment with closable front fastenings;

FIG. 6 is a perspective view of a head mounted version of the invention with a visor;

FIG. 7 is a perspective view of a head mounted version of the invention with a cap;

FIG. 8 is a perspective view of a head mounted version of the invention with an eyeglass frame;

FIG. 9 is a perspective view of a pants mounted version of the invention;

FIG. 10 is a perspective view of an alternative chest mounted version of the invention;

FIG. 11 is a perspective view of a foot mounted version of the invention;

FIG. 12 is a top plan view of a hand mounted version of the invention;

FIG. 13 is a perspective view of a linear indication member with an extruded, embedded letter E in a tapered body;

FIG. 14 is a perspective view of a linear indication member with an identifying symbol orthogonal to the long axis of the member;

FIG. 15 is a chest mounted identifying vest for conventional x-rays;

DETAILED DESCRIPTION OF THE PREFERRED EMBODIMENT (1) FIGS. 4-12, 15 and 19 illustrate a radiological imaging orientation indicator 10 providing the desired features may be constructed from the following components. As illustrated in FIGS. 1-3, 13, 14, and 16-18, a linear indication member 14 is provided. The indication member 14 has a first end 18, a second end 22 and substantially uniform cross-sectional shape 26. Means 30 are provided for positioning the indication member 14 adjacent a patient's body 34 to reliably identify the orientation of the body 34. When the linear indication member 14 is located adjacent the patient's body 34 and a sectional scanning image 36 is produced, a cross-section 40 of the indication member 14 will appear in the scanning image, indicating an orientation of the patient's body 34 with respect to the scanning image.

Figure 15A:
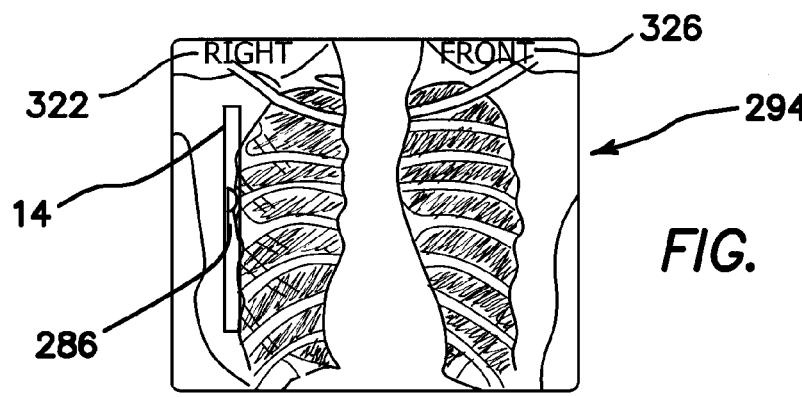
FIG. 15A is an illustration of a conventional x-ray illustrating the results of use of the FIG. 15 embodiment.

(2) In a variant of the invention, as illustrated in FIGS. 1-3, 1A-3A, 13, 14, 16 and 17, the indication member 14 is in the form of an extruded letter 38, number 42 or symbol (not shown).

(3) In another variant, as illustrated in FIG. 2, the indication member 14 is attached adjacent the patient's body 34 using means 50 selected from the group consisting of looping and hooking fasteners 54, snaps (not shown), buckles (not shown), button (not shown), zippers (not shown), elastic bands (not shown)and clips (not shown).

(4) In still another variant, as illustrated in FIG. 2A, the indication member 14 includes a first internal cavity 86. The first cavity 86 extends from a first end 18 of the member 14 to a second end 22 of the member 14 and is in the form of either of a letter 38, number 42 and symbol. When the linear indication member 14 is located adjacent the patient's body 34 and a sectional scanning image 36 is produced, a cross-section 40 of the indication member 14 and the first cavity 86 in the form of either of the letter 38, number 42 and symbol will appear in the scanning image 36, indicating an orientation of the patient's body 34 with respect to the scanning image 36.

(5) In yet another variant, the first internal cavity 86 is sealed at the first 18 and second 22 ends and includes at least one liquid 98 located in it. The liquid 98 indicates vertical orientation of the indication member 14.

Figure 16:
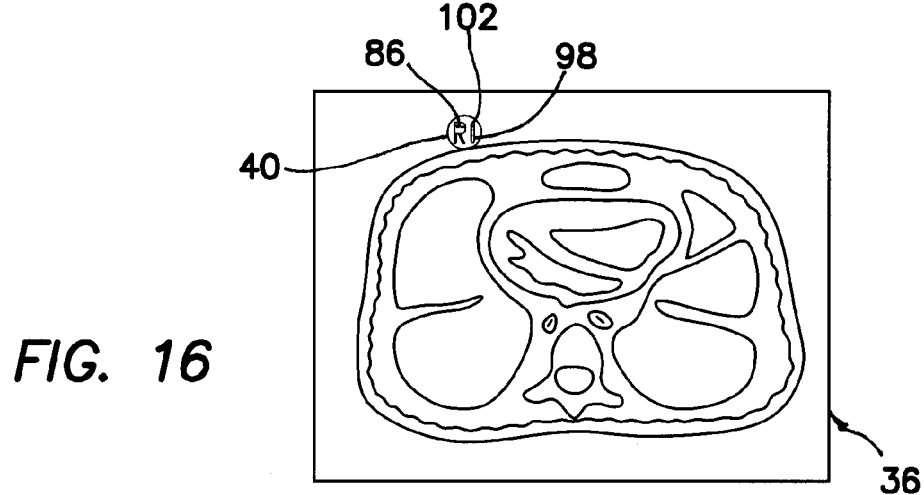
FIG. 16 is an illustration of a radiological scan of a chest portion of a body illustrating use of the FIG. 3 embodiment.

(6) In a further variant, as illustrated in FIG. 3A, the indication member 14 includes a second internal cavity 102. The second cavity 102 extends from a first end 18 of the member 14 to a second end 22 of the member 14. The second cavity 102 is partially filled with at least one liquid 98 and is sealed at the first 18 and second 22 ends to prevent loss of the liquid 98. When the linear indication member 14 is located adjacent the patient's body 34 and a sectional scanning image 36 is produced, a cross-section 40 of the indication member 14 and the second cavity 102 will appear in the scanning image, indicating an orientation of the patient's body 34 with respect to the scanning image 36, the cross-section 44 of the second cavity 102 indicating vertical orientation of the indication member 14, as illustrated in FIG. 16.

(7) In still a further variant, as illustrated in FIG. 9, the means 30 for positioning the indication member 14 adjacent the patient's body 34 includes a pair of pants 106. The pants 106 have a front closure means 110, a first side 114 and a second side 118 and are positionable upon the patient's body 34 in only a single orientation. The indication member 14 is attached to the first side 114. The pants 106 are located on the patient's body 34 with the indication member 14 positioned adjacent an identified side 122 of the patient's body 34. When the linear indication member 14 is positioned adjacent the patient's body 34 and a sectional scanning image 36 is produced, a cross-section 40 of the indication member 14 will appear in the scanning image, indicating an orientation of the patient's body 34 with respect to the scanning image 36.

(8) In yet a further variant, as illustrated in FIG. 8, the means 30 for positioning the 5 indication member 14 adjacent the patient's body 34 includes a face-mounted frame 126. The frame 126 has nose-mounted portion 130, first 134 and second 138 ear-mounted portions attached to opposite sides 142, 146 of the nose-mounted portion 130 and is positionable upon a patient's face (not shown) in only a single orientation. The indication member 14 is attached to the first ear-mounted portion 134. The face-mounted frame 126 is located on the face of 10 the patient with the indication member 14 located adjacent an identified side 122 of the patient's body 34. When the linear indication member 14 is located adjacent the patient's body 34 and a sectional scanning image 36 is produced, a cross-section 40 of the indication member 14 will appear in the scanning image 36, indicating an orientation of the patient's body 34 with respect to the scanning image 36.

(9) In another variant of the invention, as illustrated in FIGS. 4 and 5, the means 30 for positioning the indication member 14 adjacent the patient's body 34 includes a vest 158.

The vest 158 has first 162 and second 166 chest panels. The chest panels 162, 166 extend outwardly from either side of a rear centerline 170 and curve inwardly over a patient's chest 174. The first 162 and second 166 chest panels have first 178 and second 182 arm holes, 20 respectively. The indication member 14 is attached to the first chest panel 162. The vest 158 is located on the patient's body 34 with the indication member 14 located adjacent an identified side 122 of the patient's body 34. When the linear indication member 14 is located adjacent the patient's body 34 and a sectional scanning image 36 is produced, a cross-section 40 of the indication member 14 will appear in the scanning image 36, indicating an orientation of the patient's body 34 with respect to the scanning image 36.

(10) In still another variant, as illustrated in FIG. 5, the first 162 and second 166 chest panels are removably fastened together.

(11) In yet another variant, as illustrated in FIG. 10, the means 30 for positioning the indication member 14 adjacent the patient's body 34 includes a chest-mounted garment 186. The garment 186 has a front panel 190. The front panel 190 has a first side 194, a second side 198, an inner surface 202, an outer surface 206 and first 210 and second 214 arm notches. The indication member 14 is attached to the outer surface 206 at the first side 194. The chest-mounted garment 186 is located on a chest of the patient 218 with the indication member 14 located adjacent an identified side 122 of the patient's body 34. When the linear indication member 14 is located adjacent the patient's body 34 and a sectional scanning image 36 is produced, a cross-section 40 of the indication member 14 will appear in the scanning image 36, indicating an orientation of the patient's body 34 with respect to the scanning image 36.

(12) In a further variant, As illustrated in FIGS. 6 and 7, the means 30 for positioning the indication member 14 adjacent the patient's body 36 includes a head-mounted positioning device 222. The head-mounted device 222 has at least a partial head-encircling band 226. The band 226 has a first 230 portion and an opposite second portion 234 and either a cap with a bill 238 or a visor 242 attached to the band 226 between the first portion 230 and the second portion 234. Either the cap with a bill 238 or the visor 242 is aligned over a nose of the patient (not shown). The indication member 14 is attached to the first portion 230. The head-mounted positioning device 222 is located on a patient's head 250 with the indication member 14 located adjacent an identified side 154 of the patient's body 34. When the linear indication member 14 is located adjacent the patient's body 34 and a sectional scanning image 36 is produced, a cross-section 40 of the indication member 14 will appear in the scanning image 36, indicating an orientation of the patient's body 34 with respect to the scanning image 36.

(13) In still a further variant, as illustrated in FIG. 11, the means 30 for positioning the indication member 14 adjacent the patient's body 34 includes a foot-mounted positioning device 254. The foot-mounted device 254 has a foot platform 258 and a retaining upper 262 attached to the platform 258.

The upper 262 has an attachment thong 266 formed to fit between a large toe (not shown) and other toes (not shown) of only one foot of a patient (not shown). The indication member 14 is attached to the foot-mounted positioning device 254 and extends upwardly from it. The foot-mounted positioning device 254 is located on the patient's foot with the indication member 14 located adjacent an identified side 122 of the patient's body 34. When the linear indication member 14 is located adjacent the patient's body 34 and a sectional scanning image 36 is produced, a cross-section 40 of the indication member 14 will appear in the scanning image 36, indicating an orientation of the patient's body 34 with respect to the scanning image 36.

(14) In yet a further variant, as illustrated in FIG. 12, the means 30 for positioning the indication member 14 adjacent the patient's body 34 includes a hand-mounted positioning device 270. The hand-mounted device 270 has a palm cover 274, thumb opening 278 and a retaining strap 282. The strap 282 is attached across a back of a patient's hand (not shown). The hand-mounted device 270 is shaped to fit only one hand of the patient. The indication member 14 is attached to the hand-mounted positioning device 270 and extends downwardly from it. The hand-mounted positioning device 270 is located on the patient's hand with the indication member 270 located adjacent an identified side 154 of the patient's body 34. When the linear indication member 14 is located adjacent the patient's body 34 and a sectional scanning image 36 is produced, a cross-section 40 of the indication member 14 will appear in the scanning image 36, indicating an orientation of the patient's body 34 with respect to the scanning image 36.

(15) In another variant, as illustrated in FIG. 13, the indication member 14 varies in cross-sectional width from the first end 18 to the second end 22. The variation indicates a relative position of the sectional scanning image 36 with respect to the patient's body 34.

Figure 18:
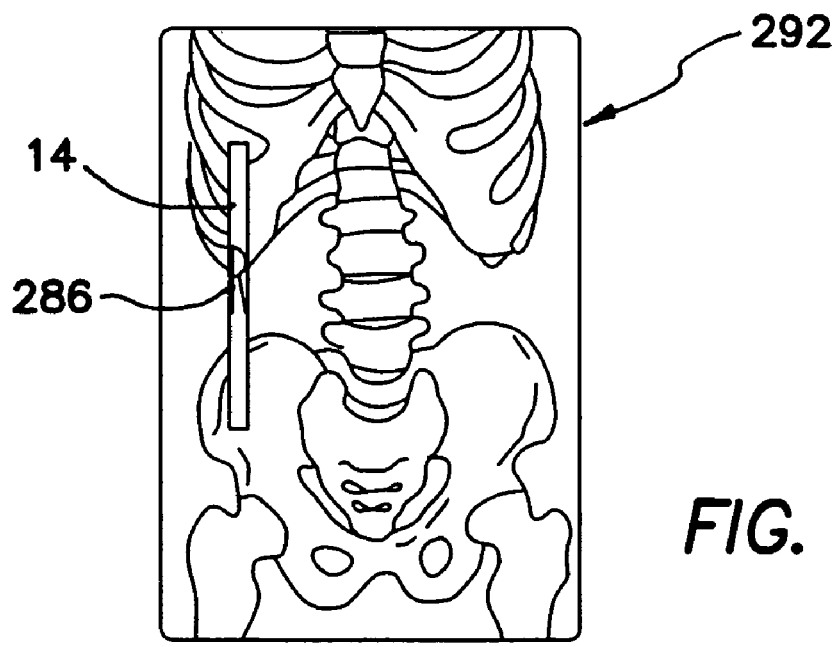
FIG. 18 is an illustration of a radiographic CT scout scan illustrating use of the FIG. 14 and FIG. 10 embodiments.

(16) In still another variant, as illustrated in FIG. 14, a two dimensional orientation symbol 286 is located orthogonally to a long axis 290 of the indication member 14. The symbol 286 appears in in either a standard radiographic image, as illustrated in FIG. 15A, or a computed tomography pilot image also known as a scout image 292, as illustrated in FIG. 18.

Figure 19:
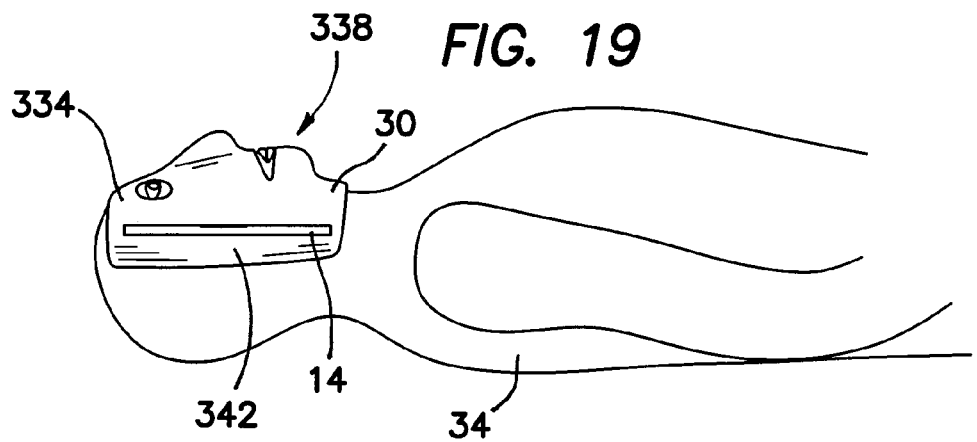
FIG. 19 is a side elevational view of a face-mounted version of the invention.
Figure 17:
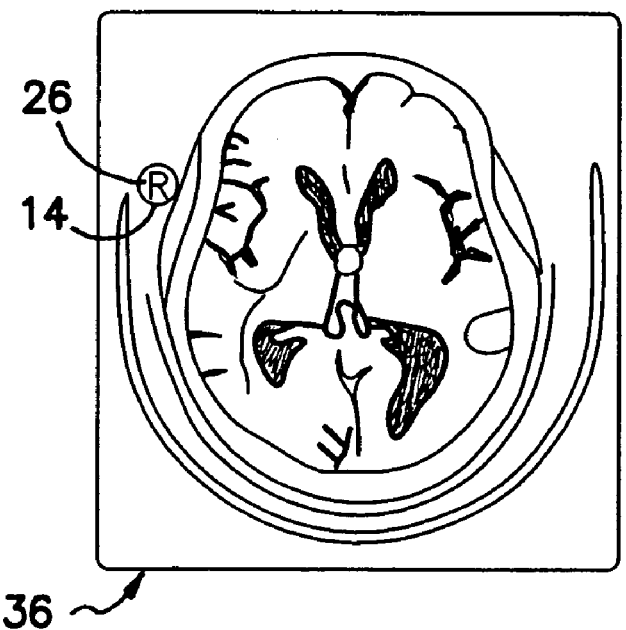
FIG. 17 is an illustration of a radiological scan of a head illustrating use of the FIG. 1 embodiment.

(17) In yet another variant, as illustrated in FIG. 19, the means 30 for positioning the indication member 14 adjacent the patient's body 34 includes a face-mounted positioning device 334. The face-mounted positioning device 334 is sized and shaped to fit over at least a portion of a face 338 of a patient 34 in only a single orientation and has a first side edge 342 and a second side edge (not shown). The indication member 14 is attached adjacent to the first side edge 342. The face-mounted positioning device 334 is located on the patient's face 338 with the indication member 14 located adjacent an identified side 154 of the patient's body 34. When the linear indication member 14 is located adjacent the patient's body 34 and a sectional scanning image 36 is produced, a cross-section 40 of the indication member 14 will appear in the scanning image 36, indicating an orientation of the patient's body 34 with respect to the scanning image 36.

(18) In a final variant, as illustrated in FIG. 15, a radiological imaging indicator 10, includes an identifying collar 298. The collar 298 has a neck recess 302, an outer surface 306, an inner surface 310, first 314 and second 318 arm notches, a body side indicator 322 and a front of body indicator 326. The indicators 322, 326 are visible on radiological images 294. The identifying collar 298 is located on a chest of the patient 330 with the inner surface 310 located against the chest 330 and the arm notches 314, 318 about arms of the patient 320. When the patient receives a chest x-ray 294, the body side indicator 322 and the front of body indicator 326 will appear in the x-ray 294, as illustrated in FIG. 15A.

The radiological imaging indicator 10 has been described with reference to particular embodiments. Other modifications and enhancements can be made without departing from the spirit and scope of the claims that follow.

The invention claimed is:

1. A radiological imaging orientation indicator, comprising:
  a singular linear indication member, said indication member has a first end, a second end and substantially uniform cross-sectional shape;
  said shape being either of an extruded letter, number and symbol;
  a face-mounted frame, said frame has nose-mounted portion, first and second ear-mounted portions attached to opposite sides of said nose-mounted portion and being positionable upon a patient's face in only a single orientation;
  said indication member being attached to said first ear-mounted portion;
  said face-mounted frame being disposed upon a face of said patient with said indication member disposed adjacent an identified side of said patient's body; and
  whereby when said linear indication member is disposed adjacent said patient's body and a sectional scanning image is produced, a cross-section of said indication member will appear in said scanning image, indicating an orientation of said patient's body with respect to said scanning image.

* * * * *